United States Patent
Bade et al.

(10) Patent No.: US 6,242,630 B1
(45) Date of Patent: Jun. 5, 2001

(54) PROCESS FOR THE CONTINUOUS PREPARATION OF 3-HALOPROPYLORGANOSILANES

(75) Inventors: Stefan Bade, Haltern; Uwe Schoen; John Burkhard, both of Rheinfelden; Franz-Michael Bollenrath, Marl; Norbert Hofmann, Bad Saeckingen; Hermann-Josef Korte, Haltern; Hartwig Rauleder, Rheinfelden; Uwe Tanger, Bochum, all of (DE)

(73) Assignee: Huels Aktiengesellschaft, Marl (DE)

( * ) Notice: Subject to any disclaimer, the term of this patent is extended or adjusted under 35 U.S.C. 154(b) by 0 days.

(21) Appl. No.: 08/908,095

(22) Filed: Aug. 11, 1997

(30) Foreign Application Priority Data

Aug. 9, 1996 (DE) ............... 196 32 157

(51) Int. Cl.⁷ ............... C07F 7/08
(52) U.S. Cl. ............... 556/479
(58) Field of Search ............... 556/479

(56) References Cited

U.S. PATENT DOCUMENTS

| | | | |
|---|---|---|---|
| 4,292,433 | * 9/1981 | Koga et al. | 556/479 |
| 4,658,050 | * 4/1987 | Quirk et al. | 556/479 |
| 5,177,236 | * 1/1993 | Seiler et al. | 556/479 |
| 5,616,762 | * 4/1997 | Kropfgans et al. | 556/479 |
| 5,663,400 | * 9/1997 | Reitmeier et al. | 556/479 |

FOREIGN PATENT DOCUMENTS

| | | |
|---|---|---|
| 28 15 316 | 3/1980 | (DE) . |
| 34 04 703 | 9/1985 | (DE) . |
| 41 19 994 | 12/1992 | (DE) . |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

A process for the continuous preparation of 3-halopropylorganosilanes of the general structure $$R_bH_{3-a-b}X_aSiCH_2CH_2CH_2Y \qquad (III),$$

where:

R is $CH_3$, $C_2H_5$, $C_3H_7$, $OCH_3$, $OC_2H_5$ or $OC_3H_7$,

X is F, Cl, Br or I,

Y is F, Cl, Br or I, and a and b are each one of the numbers 0, 1, 2 or 3 and the sum a+b is 1, 2 or 3, comprising reacting, as starting materials, an allyl halide with a silane carrying at least one H atom, wherein the starting materials are present in stoichiometric amounts or one of the starting materials is present in substoichiometric amounts, wherein the reaction carried out is a partial reaction of from 10% to 80%, on a molar basis, of the starting materials, based on either material, when both are present in stoichiometric amounts, or based on the substoichiometric material.

12 Claims, 1 Drawing Sheet

PROCESS FOR THE CONTINUOUS PREPARATION OF 3-HALOPROPYLORGANOSILANES

BACKGROUND OF THE INVENTION

1. Field of the Invention

The invention relates to a process for the continuous preparation of 3-halopropylorganosilanes of the general structure (III):

$$R_bH_{3-a-b}X_aSiCH_2CH_2CH_2Y \quad (III),$$

where:
R is $CH_3$, $C_2H_5$, $C_3H_7$, $OCH_3$, $OC_2H_5$ or $OC_3H_7$,
X is F, Cl, Br or I,
Y is F, Cl, Br or I, and where
a and b are each one of the numbers 0, 1, 2 or 3 and the sum a+b is 1, 2 or 3.

2. Description of the Background

3-Halopropylorganosilanes are important industrial intermediates in organosilane chemistry. The end products prepared from the 3-halopropylorganosilanes are employed as adhesion promoters in composite materials, e.g. in the paint and glass fiber industry, in founding and in the adhesives industry, further fields of application being elastomers and sealing compounds. Application examples are silanized glass fibers, particle reinforced plastics systems, silica-filled rubber articles, e.g. tires, the modification of hydroxyl-functionalized surfaces, substrate immobilization, silane polycondensation and constructional proofing compounds.

The preparation of 3-halopropylorganosilanes (III) is effected by preferably continuous catalyzed reaction of an allyl halide (II) with a silane (I) carrying at least one H atom and can be described by the following general reaction equation:

(1) $R_bX_aSiH_{4-a-b}$ + $CH_2CHCH_2Y$ ⟶
    (I)              (II)

$$R_bH_{3-a-b}X_aSiCH_2CH_2CH_2Y$$
(III)

This hydrosilylation reaction is always accompanied by an unwelcome side reaction which can be described by a hydrogen-halogen exchange and which gives rise to the by-product propene (V):

(2) $R_bX_aSiH_{4-a-b}$ + $CH_2CHCH_2Y$ ⟶
    (I)              (II)

$$R_bH_{3-a-b}X_aSiY + CH_2CHCH_3$$
(IV)          (V)

The propene (V) formed in this reaction is able to react further with the organosilane (I) used to give the unwelcome by-product of a propylorganosilane (VI):

(3) $R_bX_aSiH_{4-a-b}$ + $CH_2CHCH_3$ ⟶
    (I)              (V)

$$R_bH_{3-a-b}X_aSiCH_2CH_2CH_3,$$
(VI)

as a result of which the 3-halopropylorganosilane (III) yield of the preparation process is reduced in favor of the unwanted propylorganosilane (VI).

If X=Y=Cl, b=0 and a=3, this describes the preparation of 3-chloropropyltrichlorosilane (CPTCS) from trichlorosilane (TCS) and allyl chloride (AC) in analogy to the equations (1) to (3). This gives the reaction equation:

(4) $Cl_3SiH$ + $CH_2CHCH_2Cl$ ⟶ $Cl_3SiCH_2CH_2CH_2Cl$,
    (TCS)       (AC)                (CPTCS)

the side reaction equation (5) $Cl_3SiH$ + $CH_2CHCH_2Cl$ ⟶ $SiCH_4$ + $CH_2CHCH_3$ and
    (TCS)       (AC)              (STC)      (V)

the secondary reaction (6) $Cl_3SiH$ + $CH_2CHCH_3$ ⟶ $Cl_3SiCH_2CH_2CH_3$,
    (TCS)       (V)              (PTCS)

which produces the unwelcome propyltrichlorosilane (PTCS) from trichlorosilane and propene.

The reaction of allyl chloride with trichlorosilane is performed in the liquid phase, usually either on a heterogeneous catalyst or in the presence of a homogeneous catalyst.

DE 41 19 994 A1 discloses a process for preparing 3-chloropropylsilanes, in which the formation of the unwelcome by-product propylsilane is reduced, involving complex process management, by means of a preferably at least three-fold molar excess of allyl chloride. In the process, the reaction mixture containing at least allyl chloride is evaporated, condensed and then together with optionally added hydrosilane, passed over a catalyst, a stoichiometric excess of allyl chloride being maintained in the feed to the catalyst.

DE 34 04 703 A1 discloses a process for the preparation of 3-chloropropyltrichlorosilane (CPTCS) with improved yield. This involves carrying out the reaction of allyl chloride and trichlorosilane with special highly selective Pt catalysts in accordance with DE 34 04 702 A1 with simultaneous separation of propene, resulting in improved selectivity for CPTCS. The improved selectivity is essentially achieved by the use of the very expensive, special hydrosilylation catalysts according to DE 34 04 702 A1. While conventional processes require a high excess of trichlorosilane to achieve complete reaction of allyl chloride, DE 34 04 703 A1 achieves complete reaction of allyl chloride even with a small excess of trichlorosilane.

However, said excess trichlorosilane promotes, with respect to propene still present, the secondary reaction to the unwelcome by-product propyltrichlorosilane, which is also true, in general terms, for the preparation of 3-halopropylorganosilane with the unwelcome by-product propylorganosilane (VI).

SUMMARY OF THE INVENTION

It is therefore the object of the present invention to provide as simple a process as possible for the continuous preparation of 3-halopropylorganosilanes of the general structure (III) mentioned at the outset—and among these especially CPTCS and CPMDCS (3-chloropropyl-methyldichlorosilane)—in high yields on the basis even of simple, conventional catalysts, in the course of which process the formation of the unwanted propylorganosilane (VI) is suppressed as far as possible.

Surprisingly, this object is achieved by a process for the continuous preparation of 3-halopropylorganosilanes of the general structure $$R_bH_{3-a-b}X_aSiCH_2CH_2CH_2Y \qquad (III),$$

where:

R is $CH_3$, $C_2H_5$, $C_3H_7$, $OCH_3$, $OC_2H_5$ or $OC_3H_7$,

X is F, Cl, Br or I,

Y is F, Cl, Br or I, and where a and b are each one of the numbers 0, 1, 2 or 3 and the sum a+b is 1, 2 or 3, comprising reacting, as starting materials, an allyl halide with a silane carrying at least one H atom, wherein the starting materials are present in stoichiometric amounts or one of the starting materials is present in substoichiometric amounts, wherein the reaction carried out is a partial reaction of from 10% to 80%, on a molar basis, of the starting materials, based on either material, when both are present in stoichiometric amounts, or based on the substoichiometric material. Preferably, the partial reaction amounts to between 30% and 60%, based on either material, when both are present in stoichiometric amounts, or based on the substoichiometric components.

DETAILED DESCRIPTION OF THE PREFERRED EMBODIMENTS

Figure 1:
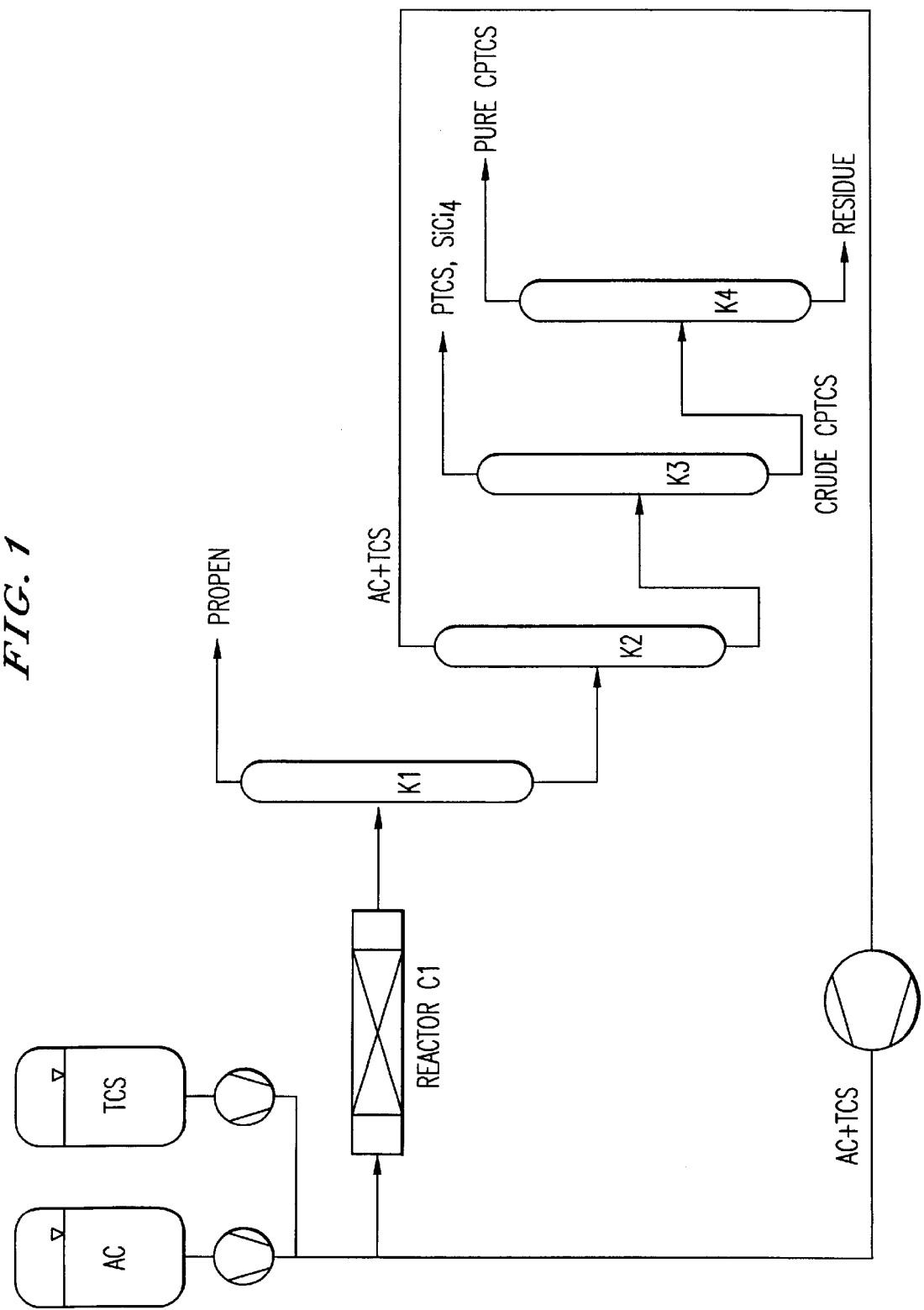
FIG. 1 is a flow diagram for a process according to the present invention.

The desired partial reaction of the starting materials is regulated in a manner known per se to those skilled in the art. Thus it is possible, if the reaction kinetics are known, to alter or regulate the partial reaction by varying the reaction temperature and/or varying the residence time of the reaction mixture in the reactor as a function of the amount used of the active metal component in the catalyst. As a result of the reaction being carried out continuously, the residence time in the reactor is then, given the constant reactor volume, defined by the mass flow rate of the starting materials. The desired partial reaction is preferentially regulated on the basis of the reaction kinetics, the amount of catalyst and a specific desired reaction temperature, by presetting the corresponding residence time.

Surprisingly, maintaining only a partial reaction of the starting materials results in an overall improvement in the yield of 3-halopropylorganosilanes. While the side reaction according to equation (2), which always occurs in parallel, takes place to approximately the same extent, the secondary reaction of the propene, which is formed in the side reaction, with the silane used is repressed, because of the only partial reaction of the starting materials and the concomitant higher availability of allyl halide, so that the formation of the unwelcome by-product propylorganosilane (VI) declines and the yield of useful product increases.

This result can be further improved by the propene formed in the side reaction being separated from the reaction mixture, thus further reducing the secondary reaction. The separation of the propene can take place simultaneously in the reactor or downstream of the reactor by means of at least one separation stage.

While, according to the invention, the molar ratio of the starting materials silane to allyl halide can be between about 0.5 and 1.5, preference is given, however, to employing a moderate excess of the allyl halide. This is because it was also found that the secondary reaction of silane used with existing propene can also be repressed by an increase in the allyl halide concentration in the starting material feed (and thus in the reaction admixture). It is therefore advantageous for the use of an allyl halide excess to be combined with the previous measures, the preferred allyl halide excess being distinctly lower than the preferred allyl chloride excess, described in DE 41 19 994 A1, of at least 3:1.

The process according to the invention can be carried out with homogeneous or heterogeneous catalysis. Suitable, in general, are all known catalysts for congeneric reactions, including simple catalysts, in particular. Heterogeneous catalysts are preferred because of the advantage provided by easy separability. According to the invention preference is given to the use of a simple heterogeneous Pt catalyst on activated carbon, which contains between 0.01 and 1 wt % of Pt. The reaction temperature as a rule is between 60 and 160° C. preferably between 80 and 140° C. The pressure usually is between 0 and 2 MPa absolute, preferably between 0.3 and 1.4 MPa absolute, to keep the starting materials in the liquid phase.

Suitable reactors according to the invention are all the conventional reaction apparatuses, familiar to those skilled in the art, for homogeneous reactions in the liquid phase such as e.g. stirred vessels, loop reactors etc. or reactors for liquid-solid-contacts such as eg. fixed-bed reactors. The choice of reactor is determined by the conditions (including the catalyst selected) defined by the reaction in each individual case.

As already mentioned, the first step preferably is at least to separate propene from the reaction mixture or product mixture. The aim is to remove propene as completely as possible. The remaining reaction product mixture can then be split, in a further preferred embodiment of the novel process, into the useful product, unwelcome by-products and unreacted starting materials, the unreacted starting materials preferably being recycled to the reactor. The separation of the product mixture is carried out e.g. by distillation, in a manner known to those skilled in the art. Alternatively, however, the separation of the propene may take place indirectly, rather than systematically, as a result of the useful product and optionally unreacted starting materials being separated from the product mixture. Separated propene is preferably utilized in a suitable way, e.g. by allyl halide being prepared from it.

The preferred embodiments, in particular, of the novel process are distinguished by a most substantial utilization of the starting materials for the conversion into useful product and by high economic efficiency. The major part of the products other than useful products is reutilized by processing and recycling; the amount of unwanted products resulting from the side reaction and secondary reaction is minimized by the partial reaction of the starting materials, the preferential separation of propene and the preferential use of an allyl halide excess. Overall it is thus possible to achieve selectivities of about 75%, improved by about 10%, on the basis of the reacted allyl halide. Further improvements in selectivity and yield can be achieved, starting from the novel process, by the use of special catalyst systems (compare eg. DE 34 04 703 A1). As a result of the reaction temperatures, preferentially maintained according to the invention, of less than 140° C. which preferably are not exceeded even in the course of the products being worked up, the product mixture is very largely free from other impurities, unless these have been introduced with the starting materials in the first place.

In particular, the proportion of high-boiling components which can be formed at high temperatures, eg. by oligomerization of the allyl halide or by disproportionation of the silane produced, with corresponding secondary reactions, in the product mixture is only 0.1 wt % or less, as long as the starting materials are free from high-boiling components.

A further advantage of the novel process, compared with processes carried out with homogeneous catalysts or suspension catalysts (compare eg. DE 34 04 703 A1), is that the use of a heterogeneous catalyst will not result in losses in activity owing to losses of catalyst. In the case of homogeneous or suspension catalysts used in a continuous process, catalyst is steadily being dragged out, so that the costs for the catalyst are higher than with a heterogeneous catalysis mode of operation.

The process according to the invention, with its simple process control mechanism, is described below in more detail in a preferred embodiment for the example of the preparation of 3-chloropropyltrichlorosilane (CPTCS) from trichlorosilane (TCS) and allyl chloride (AC), without being limited thereto. Preferably, according to the invention even the continuous preparation of CPTCS is carried out by TCS being reacted with AC at reaction temperatures of between 60° C. and 160° C., particularly preferably at reaction temperatures of between 80 and 140° C., the residence time of the reaction mixture in the reactor being between 1 min and 500 min, preferably between 10 min and 200 min, in order to achieve, according to the invention, a partial reaction of the starting materials of from 10% to 80%, preferably from 30% to 60%, based on the substoichiometric component. The molar ratio of TCS to AC in the starting material stream is preferably between about 0.5 and 1.5, an AC excess being particularly preferred. FIG. 1 shows the corresponding process flow diagram.

For the purpose of hydrosilylation use is made e.g. of a stirred-tank reactor or fixed-bed reactor (C1), in which the partial reaction according to the invention of between 10 and 80%, preferably between 30 and 60% of the starting materials, based on the substoichiometric component, is regulated via the reaction temperature and the residence time. Downstream of the reactor there is a separator stage K1 in which the propene formed as a by-product is separated. This prevents the propene from reacting with the trichlorosilane, in a secondary reaction, to form the unwelcome by-product propyltrichlorosilane.

The partially reacted reaction mixture from the hydrosilylation reaction then passes, after the propene separation (K1), into the separation stage K2 in which the unreacted starting materials allyl chloride and trichlorosilane are separated as low-boiling components and, by means of a circulating pump, are recycled to the hydrosylation reactor C1. The stream of high-boiling components from K2 passes into the separation stage K3, in which the byproducts propyltrichlorosilane and $SiCl_4$ are separated as low-boiling components and the crude product 3-chloropropyltrichlorosilane is drawn off as the bottom product. The crude product finally undergoes fine purification in the separation stage K4, after which the product 3-chloropropyltrichlorosilane is obtained as a pure product having a purity of >99.9 mol %. Fine purification, which is preferably carried out by rectification and particularly preferably by vacuum rectification of the product, serves for the separation of other impurities which e.g. may still originate from the starting materials.

The hydrosilylation reactor C1 starting material feed stream comprising allyl chloride and trichlorosilane is preferably metered in with a flow rate and the ratio being controlled. To this end, firstly, the composition and the magnitude of the recycle stream of allyl chloride and trichlorosilane is measured on line, and secondly the results of these measurements are used to meter the fresh starting materials allyl chloride and trichlorosilane from the reservoirs. This ensures that a starting material stream of constant magnitude and constant composition is fed to the hydrosilylation reactor. According to the invention this provides the advantage that compared with conventional processes, considerably smaller amounts of unwanted component in the form of propyltrichlorosilane are formed. While about the same amount of $SiCl_4$ is formed, since the formation proceeds in parallel with that of CPTCS, it is possible to suppress the secondary reaction (6) by partial reaction of the starting materials, by an increase in the AC concentration (AC excess) and by the separation of propene. As a result, less $SiHCl_3$ is converted into the unwanted product PTCS. Moreover, higher space-time yields can be achieved than in conventional processes, with a distinctly higher molar ratio of 3-chloropropyltrichlorosilane to propyltrichlorosilane. In conventional processes, which are characterized by a high final conversion ratio of allyl chloride, the molar ratio of CPTCS to PTCS in the product is only about 3.5, whereas in the novel process the ratio as a rule is distinctly greater than 4, in some cases even greater than 100. The space-time yields achievable with the novel process are up to 100 mol of $CPTCS/(h \cdot g_{Pt})$ even at a reaction temperature of 100° C. In the Examples 1 and 2, described below in more detail, which are each carried out at a reaction temperature of 80° C., the space-time yields are 22.6 and 40.25 mol of $CPTCS/(h \cdot g_{Pt})$, respectively. In DE 41 19 994 A1 (Example 6), the space-time yield is only 1.61 mol of $CPTCS/(h \cdot g_{Pt})$, in DE 34 04 703 A1 even between only 0.18 mol of $CPTCS/(h \cdot g_{Pt})$ (100° C., Example 1) and 0.52 mol of $CPTCS/(h \cdot gt,)$ (100° C., Example 6). Those skilled in the art and aware of this preferred process design will be able to conceive other embodiments of the process for the preparation of CPTCS.

In a manner similar to the preparation of CPTCS, the novel process can also be used for the preparation of 3-chloropropyl-methyldichlorosilane (CPMDCS) from methyldichlorosilane (MDCS) and allyl chloride (AC), the reaction temperature between 60° C. and 160° C. and the residence time of the reaction mixture in the reactor being between 1 min and 500 min, preferably between 10 min and 200 min.

Having generally described this invention, a further understanding can be obtained by reference to certain specific examples which are provided herein for purposes of illustration only and are not intended to be limiting unless otherwise specified.

EXAMPLE 1

Reaction of trichlorosilane ($SiHCl_3$) with allyl chloride to give 3-chloropropyltrichlorosilane with 80% reaction without separation of propene In a continuous loop reactor with external loop (reactor volume 1000 ml, catalyst volume 120 ml) $SiHCl_3$ (TCS) and allyl chloride (AC) are reacted at a reaction temperature of 80° C. to give 3-chloropropyltrichlorosilane (CPTCS). The molar feed ratio of TCS:AC is 1.2; propene is not separated and the reaction of AC is set to 80%. The mass of the catalyst (0.1 wt % of Pt on activated carbon) is 45 g. The loop flow rate is 60 l/h, the contact time on the catalyst therefore being 7.2 sec.

The pressure in the reactor is 3.3 bar gauge. The volume flow at the inlet of the reactor is 0.343 l/h and consists of TCS and AC (TCS: 205 ml/h, AC: 138 ml/h). The mean residence time in the reactor is therefore 175 min. The following table illustrates the molar composition of the input and output steam.

| Component | Input mol % | Output mol % |
| --- | --- | --- |
| x(Trichlorosilane) | 0.5454 | 0.188 |
| x(Allyl chloride) | 0.4545 | 0.1365 |
| x(Silicon tetrachloride) | 0 | 0.134 |
| x(Propyltrichlorosilane) | 0 | 0.0842 |
| x(3-Chloropropyltrichlorosilane) | 0 | 0.4074 |
| x(Propene) | 0 | 0.0499 |

The molar flow rates of the Si components at the input and output are:

| Component | Molar input flow rate mol/h | Molar output flow rate mol/h |
| --- | --- | --- |
| Trichlorosilane | 2.03 | 0.47 |
| 3-Chloropropyltrichlorosilane | 0 | 1.02 |
| Propyltrichlorosilane | 0 | 0.21 |
| Silicon tetrachloride | 0 | 0.33 |

The molar ratio of CPTCS to PTCS is therefore 4.85, the production output being 216 g of CPTCS/h while 37 g of PTCS/h are produced at the same time. In this example it is only by the partial reaction of the allyl chloride that the product ratio is shifted in favor of CPTCS. The reacted TCS gives rise to 65.4% of CPTCS, 13.5% of PTCS and 21.1% of $SiCl_4$.

After the product mixture leaving the reactor is separated, 47 ml/h of TCS and 27 ml/h of AC are recycled by means of a pump to the reactor inlet and supplemented with fresh starting materials; volume flows of 158 ml/h for TCS and of 111 ml/h for AC are required to restore the molar ratio TCS:AC of 1.2.

EXAMPLE 2

Reaction of trichlorosilane ($SiHCl_3$) with allyl chloride to give 3-chloropropyltrichlorosilane with 50% reaction and continuous separation of propene In a continuous loop reactor with external loop (reactor volume 1000 ml, catalyst volume 120 ml) $SiHCl_3$ (TCS) and allyl chloride (AC) are reacted at a reaction temperature of 80° C. to produce 3-chloropropyltrichlorosilane (CPTCS). The molar feed ratio of AC:TCS is 1.2; propene formed is continuously separated during operation by being stripped with nitrogen. The reaction of TCS is set to 50%. The mass of the catalyst (0.1 wt % of Pt on activated carbon) is 45 g. The loop flow rate is 60 l/h, the contact time on the catalyst therefore being 7.2 sec.

The pressure in the reactor is 4.1 bar gauge. The volume flow at the inlet of the reactor is 1.0 l/h and consists of TCS and AC (TCS: 507 ml/h, AC: 493 ml/h). The mean residence time in the reactor is therefore 60 min. The following table illustrates the molar composition of the input and output stream.

| Component | Input mol % | Output mol % |
| --- | --- | --- |
| x(Trichlorosilane) | 0.4545 | 0.2732 |
| x(Allyl chloride) | 0.5454 | 0.3994 |

-continued

| Component | Input mol % | Output mol % |
| --- | --- | --- |
| x(Silicon tetrachloride) | 0 | 0.0663 |
| x(Propyltrichlorosilane) | 0 | 0.0151 |
| x(3-Chloropropyltrichlorosilane) | 0 | 0.2015 |
| x(Propene) | 0 | 0.0446 |

The molar flow rates of the Si components at the input and output are:

| Component | Molar input flow rate mol/h | Molar output flow rate mol/h |
| --- | --- | --- |
| Trichlorosilane | 5.06 | 2.53 |
| 3-Chloropropyltrichlorosilane | 0 | 1.31 |
| Propyltrichlorosilane | 0 | 0.13 |
| Silicon tetrachloride | 0 | 0.59 |

The molar ratio of CPTCS to PTCS is therefore 13.3, the production output being 384 g of CPTCS/h while 23 g of PTCS/h are produced at the same time. Compared with Example 1, the AC excess, the separation of propene and the reduced conversion ratio in the reactor gives rise to a distinct increase in the selectivity. The amount of the unwelcome by-product PTCS is drastically reduced. The reacted TCS gives rise to 71.5% of CPTCS, 5.2% of PTCS and 23.3% of $SiCl_4$.

After the product mixture leaving the reactor is separated, 255 ml/h of TCS and 295 ml/h of AC are recycled by means of a pump to the reactor inlet and supplemented with fresh starting materials; volume flows of 252 ml/h for TCS and of 198 ml/h for AC are required to restore the molar ratio AC:TCS of 1,2.

The following table summarizes the selectivity results with respect to the reacted TCS from Examples 1 and 2:

| Component | Selectivity Example 1 | Selectivity Example 2 |
| --- | --- | --- |
| CPTCS | 65.4% | 71.5% |
| PTCS | 13.5% | 5.2% |
| $SiCl_4$ | 21.1% | 23.3% |

The advantages of the novel process in its preferred embodiments have thus been clearly documented.

The disclosure of priority application German 196 32 157.3, filed Aug. 9, 1996, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the continuous preparation of 3-halopropylorganosilanes of the general structure $$R_bH_{3-a-b}X_aSiCH_2CH_2CH_2Y \qquad (III),$$

where:
  R is $CH_3$, $C_2H_5$, $C_3H_7$, $OCH_3$, $OC_2H_5$ or $OC_3H_7$,
  X is F, Cl, Br or I,
  Y is F, Cl, Br or I, and a and b are each one of the numbers 0, 1, 2 or 3 and the sum a+b is 1, 2 or 3, comprising reacting, as starting materials, an allyl halide with a silane carrying at least one H atom, wherein the starting materials are present in stoichiometric amounts or one of the starting materials is present in substoichiometric amounts, wherein the reaction carried out is a partial reaction of from 10% to 80%, on a molar basis, of the starting materials, based on either material, when both are present in stoichiometric amounts, or based on the substoichiometric material.

2. The process as claimed in claim 1, wherein the reaction carried out is a partial reaction of from 30% to 60%, on a molar basis, of the starting materials, based on either material, when both are present in stoichiometric amounts, or based on the substoichiometric material.

3. The process as claimed in claim 1, wherein propene formed as a by-product is separated.

4. The process as claimed in claim 1, wherein the molar ratio of silane to allyl halide is between 0.5 and 1.5.

5. The process as claimed in claim 4, wherein the molar ratio of silane to allyl halide is between 0.5 and 1.

6. The process as claimed in claim 1, wherein unreacted starting materials are separated from a product mixture and are recycled into the reaction.

7. The process as claimed in claim 1, wherein the reaction is performed by heterogeneous catalysis.

8. The process as claimed in claim 1, wherein the reaction is performed in the liquid phase at a temperature of between 60° C. and 160° C.

9. The process as claimed in claim 8, wherein the reaction is performed in the liquid phase at a temperature of between 80° C. and 140° C.

10. The process as claimed in claim 1, additionally comprising presetting the reaction temperature and/or the residence time of the reaction mixture in the reactor.

11. The process as claimed in claim 1, wherein the 3-halopropylorganosilane is 3-chloropropyltrichlorosilane and the silane is trichlorosilane, the reaction is carried out at a temperature of between 60° C. and 160° C. and a residence time of the reaction mixture in the reactor of between 1 min and 500 min.

12. The process as claimed in claim 1, wherein the 3-halopropylorganosilane is 3-chloropropyl-methyldichlorosilane and the silane is methyldichlorosilane, the reaction is carried out at a temperature of between 60° C. and 160° C. and a residence time of the reaction mixture in the reactor of between 1 min and 500 min.

* * * * *